United States Patent
Dho et al.

[11] Patent Number: 6,127,569
[45] Date of Patent: Oct. 3, 2000

[54] CRYSTALLIZATION OF α-L-ASPARTYL-L-PHENYLALANINE METHYL ESTER

[75] Inventors: Hwa Jung Dho, Kyungki-do; Heon Yong Eohm, Seoul; Kyung Eun Choi, Kyungki-do; Bun Sam Lim, Seoul, all of Rep. of Korea

[73] Assignee: Daesang Corporation, Seoul, Rep. of Korea

[21] Appl. No.: 09/183,436

[22] Filed: Oct. 30, 1998

[30] Foreign Application Priority Data

Jul. 29, 1998 [KR] Rep. of Korea ................. 98-30675

[51] Int. Cl.$^7$ .................................................. C07C 229/00
[52] U.S. Cl. .......................................................... 560/41
[58] Field of Search ................................................ 560/41

[56] References Cited

U.S. PATENT DOCUMENTS

| | | |
|---|---|---|
| 5,041,607 | 8/1991 | Naruse et al. . |
| 5,097,060 | 3/1992 | Naruse et al. . |
| 5,502,238 | 3/1996 | Rijkers et al. . |
| 5,543,554 | 8/1996 | Ohura et al. . |
| 5,621,137 | 4/1997 | Naruse et al. . |
| 5,637,754 | 6/1997 | Rijkers et al. . |
| 5,744,632 | 4/1998 | Naruse et al. . |

FOREIGN PATENT DOCUMENTS 523 813 A1  1/1993  European Pat. Off. .

*Primary Examiner*—Samuel Barts
*Attorney, Agent, or Firm*—Knobbe, Martens, Olson & Bear, LLP

[57] ABSTRACT

Disclosed is a method of crystallizing α-L-aspartyl-L-phenylalanine methyl ester, which is a sweetening agent substituting sugar and commonly referred to as aspartame. An aspartame solution is sprayed and droplets of the solution fall downward. Cold airflow is blown to the falling droplets of the aspartame solution to cool them. The aspartame dissolved in the droplets crystallizes, and the slurry including the aspartame crystals and the remaining solution is collected for further processes. Also disclosed is a crystallizer for cooling crystallizing the aspartame solution with this method. The crystallizer has an atomizer for spraying the aspartame solution supplied thereto and an air inlet and an air outlet. The cold air is blown into the crystallizer through the air inlet, cools the droplets of the aspartame solution, and is discharged through air outlet.

19 Claims, 2 Drawing Sheets

CRYSTALLIZATION OF α-L-ASPARTYL-L-PHENYLALANINE METHYL ESTER

BACKGROUND OF THE INVENTION

1. Field of the Invention

The present invention relates to producing a low-calorie sweetening substance, more particularly, to crystallization of the α-L-aspartyl-L-phenylalanine methyl ester.

2. Description of the Related Technology

α-L-aspartyl-L-phenylalanine methyl ester, hereinafter referred to as aspartame, is a low-calorie sugar substitute and is industrially synthesized by several different processes. The synthesized aspartame is isolated most commonly by crystallization, which is followed by dewatering and drying processes. Further treatments or processes can be applied to the aspartame to provide various consumer products.

Crystallization occurs by cooling a solution or by evaporating the solvent thereof. In cooling crystallization, as the solution is cooled, the solute is supersaturated, which causes formation and growth of crystals. Generally, obtaining coarse and uniform crystals is the goal. In theory, this can be accomplished by cooling the solution with an infinitesimal amount of heat transfer.

In U.S. Pat. No. 5,543,554, a method of cooling crystallization is disclosed. An aspartame solution is conductively cooled within a crystallizer without any forced agitation or stirring. The obtained crystals of the aspartame are coarse and uniform, which is desirable. However, since no forced flow is utilized in the cooling crystallization of the aspartame, the crystals obtained within the crystallizer are not easily discharged and it takes a relatively long period of time.

In European Patent Application Laid-Open 523,813 A, an aspartame solution is directly contacting with ice to cool and crystallize the aspartame. The process can reduce the time required in the cooling crystallization. However, as the ice is melting, the aspartame solution is diluted and the final yield of the aspartame crystals decreases.

In U.S. Pat. No. 5,502,238, an alternative method of crystallizing an aspartame is disclosed. This method uses the solubility changes of the aspartame, depending on pH of the solution. However, since acidic solution of the aspartame is neutralized at a relatively high temperature, the aspartame may break down and produce a byproduct such as benzyl-3,6-dioxo-2-piperazine acetic acid (DKP).

There is thus a need for an alternative or improved method of crystallizing aspartame.

SUMMARY OF THE INVENTION

One aspect of the present invention provides a method of crystallizing a solute dissolved in a solution. According to the method, an aqueous solution is prepared, and cold air is blown to form a layer of cold airflow. The solution is atomized to droplets, which pass through the layer of cold air flow, thereby crystallizing the solute dissolved in the droplets. The slurry including the solute crystals and remaining solution is accordingly obtained.

Another aspect of the present invention provides a crystallizer for crystallizing a solute dissolved in a solution. The crystallizer comprises a crystallization chamber and an atomizer installed within the crystallizer. The crystallization chamber comprises a solution inlet port for introducing the solution into the chamber, an air inlet opening for introducing a cold airflow into the chamber, an air outlet opening, and a slurry outlet port. The atomizer is connected to the solution inlet port and atomizes the solution to droplets of the atomized solution and disperses the droplets over the cold airflow. The droplets heat-exchange with the cold airflow to crystallize the solute dissolved in the droplets and form slurry comprising crystals and remaining solution while they pass through the airflow introduced into the chamber. The slurry is discharged through the slurry outlet port, and the airflow after the heat-exchange is discharged through the air outlet opening.

DETAILED DESCRIPTION OF THE PREFERRED EMBODIMENT

The inventors of this application researched alternative ways of crystallization of the aspartame. The research showed the possibility of cooling crystallizing by contacting cold air to an aspartame solution. It is also discovered that providing the aspartame solution in an atomized form, i.e., dispersing droplets of the solution, facilitates the cooling crystallization of the aspartame with the cold air. The present invention to be further discussed herein in detail is based on these research results.

Figure 1:
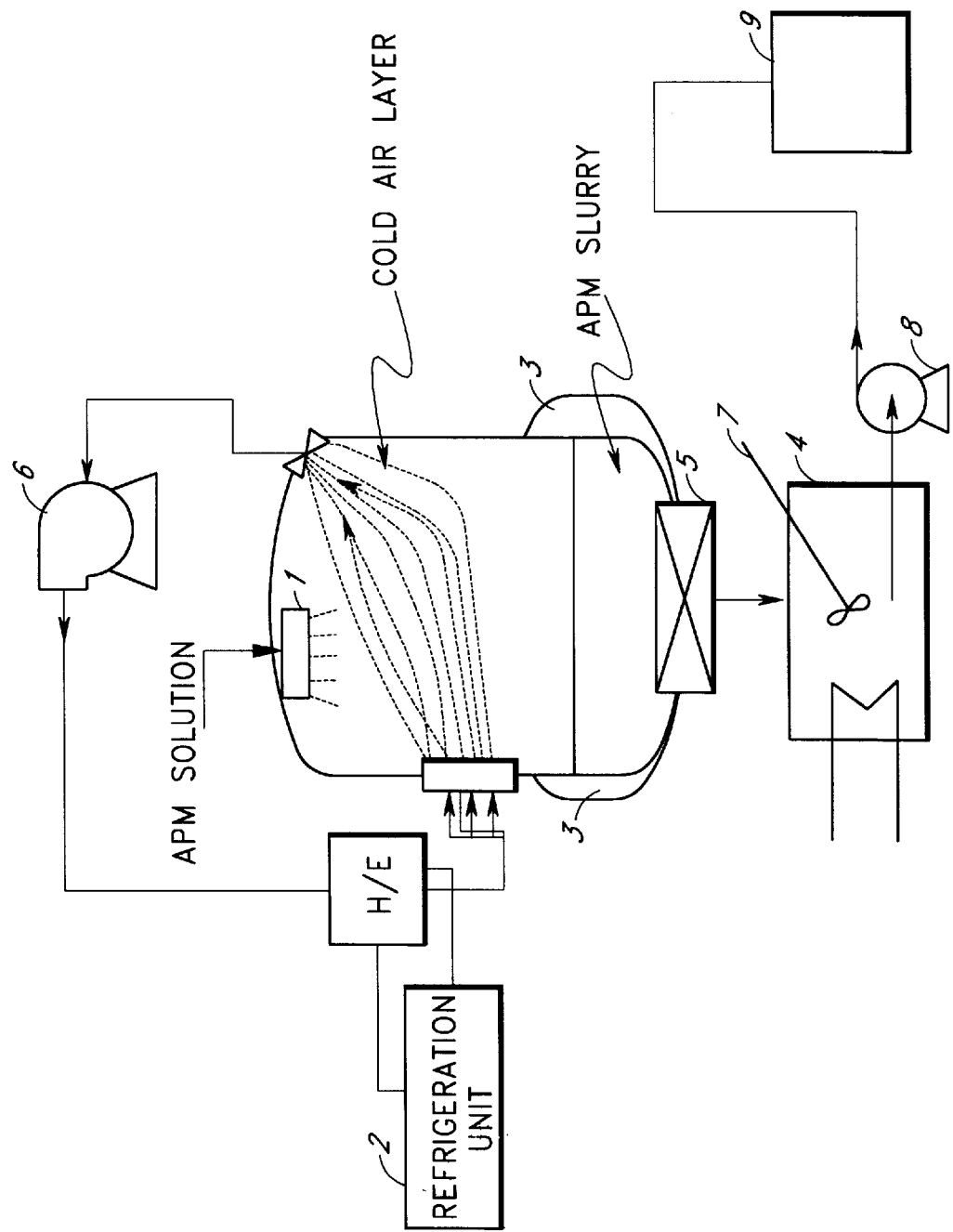
FIG. 1 is a schematic illustration of a crystallizer and related equipment in accordance with one embodiment of the present invention.

A cooling crystallizer in accordance with the present invention is illustrated in FIG. 1. Provided is a crystallization chamber 10, including an inlet 12 for introducing aspartame solution into the chamber 10 and an outlet 14 for discharging aspartame slurry. Here, the slurry means the result of the crystallization of the aspartame solution and includes aspartame crystals and remaining solution with a lower aspartame concentration than the initial aspartame solution supplied through the inlet 12.

The aspartame solution, passing through the inlet 12, is supplied to an atomizer 16 for spraying the solution. The inlet 12 is advantageously located on a top wall of the chamber 10 to facilitate the supply of the solution to the atomizer 16. On the other hand, the aspartame slurry outlet 14 is advantageously formed on a bottom wall of the chamber, such as on the bottom wall to facilitate the discharge of the slurry.

The chamber 10 further has an air inlet opening 18 and an air outlet opening 20. The air inlet opening 18 is formed on a sidewall of the chamber 10 to introduce cold air into the chamber 10. The air inlet opening 18 is advantageously located at a little lower level than the atomizer 16. The air outlet opening 20 is formed on the sidewall of the chamber 10 to discharge the air which has passed through the chamber 10. The air outlet opening 20 is advantageously located on the opposite side of the air inlet opening 18 and at a higher level than the air inlet opening 18.

Aqueous aspartame solution supplied to the atomizer 16 is sprayed or dispersed to droplets of the aspartame solution, which fall down within the chamber 10. Meanwhile, cold air, which is cooled outside the chamber 10, is introduced into the chamber 10 to cool the falling aspartame solution droplets. The cold air is blown from the air inlet opening 18 and flows toward the air outlet opening so that a layer 22 of cold air flow is formed under the atomizer 16 within the crystallization chamber 10.

When the falling droplets of the aspartame solution meet the layer 22 of cold air flow, heat exchange occurs between the cold air and the droplets of the solution. As the droplets become cool and the aspartame dissolved in the droplets is supersaturated and finally crystallized. The crystallized aspartame and the remaining solution settle and form aspartame slurry in the lower part of the chamber 10, which will be discharged through the slurry outlet 14. To avoid uncontrolled heat transfer, the walls of the chamber 10 is advantageously heat insulated.

The aspartame slurry can be additionally cooled to further crystallize the aspartame, which still remains dissolved in the slurry, before it is discharged from the chamber 10. For this further cooling, a lower portion of the chamber 10 is advantageously equipped with cooling jacket 23, within which a coolant is circulating. Additionally, the aspartame slurry may be further cooled outside the chamber 10 with forced flow or agitation, which can facilitate the separation of solid crystals from the remaining solution in the slurry in the following process of dewatering. Alternatively, the aspartame slurry is first discharged and further cooled outside the chamber 10, where a forced flow or agitation may be applied.

The cold air introduced into the chamber 10 becomes warm as it heat-exchanges with the aspartame droplets while it flows toward the air outlet opening 20, which is opposingly located to the air inlet opening 18. A fan 24 is advantageously provided next to the air outlet opening 20 to suck and expel the heat-exchanged air from the chamber 10. Advantageously, the expelled air is in turn cooled in a heat exchanger 26 connected to an outside refrigeration system 28 and returns to the crystallization chamber 10 to cool the aspartame droplets.

The aspartame crystals obtained in accordance with the present invention are generally coarser than those obtained by cooling the aspartame solution itself. Further, the structure of the crystals is such that water retained in the structure is easily removed by centrifugation or pressurized filtration in the following process.

Solvent used in the aspartame aqueous solution supplied to the crystallizer includes water or a mixture of water and a water-miscible organic solvent. The mixed solvent advantageously dissolves the aspartame more than water itself. Lower alcohol, such as methanol, ethanol, isopropanol, or t-butanol are advantageously used as the water miscible organic solvent when the solvent is removed after the crystallization by evaporation under vacuum condition.

Before the crystallization, the aspartame aqueous solution is heated to adjust the concentration high enough to obtain a decent amount of aspartame crystals during the cooling crystallization. The aspartame solution is heated until aspartame begins to break down and form benzyl-3,6-dioxo-2-piperazine acetic acid or α-L-aspartyl-L-phenylalanine, which is at about 70° C. The initial temperature of the aspartame solution supplied to atomizer 16 is advantageously from about 40° C. to about 70° C. Desirably, the solution is supplied to the atomizer 16 at from about 50° C. to about 60° C. The aspartame concentration is advantageously higher than about 90% of the saturated concentration at the temperature.

Any nozzle or spray to disperse liquid can be used as an atomizer in accordance with the present invention. For example, a pressure nozzle, rotatory nozzle, spray nozzle, etc. can be used. The atomizer is advantageously located right above the top of the cold airflow layer 22. The size of the atomized droplets in diameter is advantageously from about 0.01 mm to about 2 mm, desirably from about 0.02 mm to about 1 mm, preferably from about 0.02 mm to about 0.5 mm. The aspartame solution is atomized and sprayed at a constant rate. The sprayed aspartame solution passes the layer 22 of cold airflow advantageously within about 1 min., preferably, from about 2 sec. to about 30 sec.

Any gas, which does not react with the aspartame as well as the solvent, can be used in cooling the falling droplets of the aspartame solution. Advantageously, atmospheric air, nitrogen gas, or inert gases are used. The cold air is blown into the chamber at a temperature from about −5° C. to about 50° C., advantageously from about 0° C. to about 20° C. The temperature of the cold air is preferably adjusted so that it is a little cooler than that of the droplets sprayed in the atomizer.

The layer 22 of the cold airflow is thick enough the aspartame droplets to heat-exchange with the cold air while they are passing through the layer 22. Advantageously, the layer 22 of the cold airflow is thicker than about 0.5 m. The thickness of the cold airflow layer 22 is desirably from about 1 m to about 4 m, and preferably from about 1 m to about 2.5 m thick. The cold air is blown through the chamber advantageously at a constant speed. The speed of the cold air is adjusted so that the cold airflow does not agitate the falling aspartame solution droplets. Advantageously, the cold airflow is not faster than the falling droplets.

Figure 2:
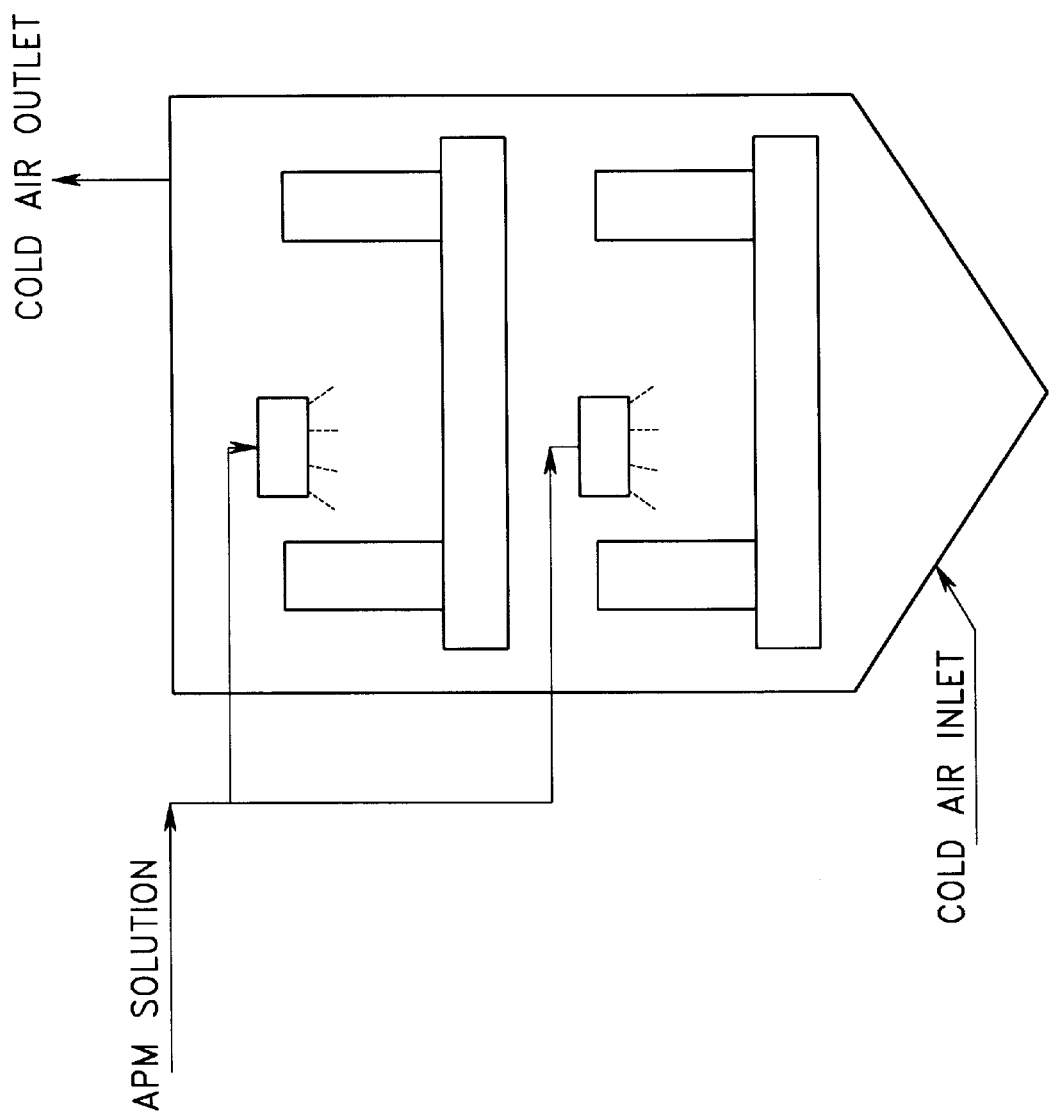
FIG. 2 is also a schematic illustration of a crystallizer in accordance with another embodiment of the present invention.

FIG. 2 illustrates a crystallization chamber 10 in accordance with another embodiment of the present invention. Like elements are referred by like numerals, and the foregoing description of like components between the embodiments should be understood to apply to the present embodiment unless indicated otherwise.

A plurality of atomizers 16a, 16b are installed at different levels within the chamber 10. An air inlet opening 18 advantageously is formed on a sidewall of the chamber 10 at a level lower than the lowest atomizer 16b. An air outlet opening 20 is advantageously provided on a sidewall or top wall of the chamber 10 at a level higher than the highest atomizer. A partition 30 is provided under each atomizer 16a, 16b such that each partition 30 covers at least the below-located atomizer 16b. Advantageously, the partition 30 is slanted toward any direction with a substantially flat top surface to facilitate the flow of the slurry thereon. Alternatively, the top surface of the partition 30 is radially outwardly slanted down. Although not illustrated, an above-located partition is advantageously broader than a below-located partition.

Aspartame solution is atomized and sprayed downward at each atomizer 16a, 16b. Cold air is blown upward from the air inlet opening 18 and cools aspartame droplets falling between each atomizer 16*a*, 16*b* and partition 30. The air thereafter is discharged from the chamber 10 through the air outlet opening 20. Aspartame is crystallized while the droplets are heat exchanging with the cold air, and aspartame slurry falls on each partition 30, which avoids the slurry attacking the below-located atomizer 16*b* and the sprayed droplets therefrom. The aspartame slurry slides down on the slanted top surface of the partition 30 and falls to the bottom portion of the chamber 10, where a slurry discharge outlet 38 is formed.

Alternatively, the plurality of atomizers can be arranged horizontally rather than vertically as described above. With the horizontally arranged plurality of atomizers, the partitions 30 can be removed from the crystallization chamber 10.

The present invention will now be further described by examples.

EXAMPLE 1

4.8 wt % of aspartame water solution at 55° C. was supplied to a nozzle installed at an upper portion within a stainless steel crystallizer as shown in FIG. 1. The nozzle sprayed the aspartame solution to droplets with a diameter from about 0.1 mm to about 0.12 mm. Cold air cooled to 0° C. was blown into the crystallizer to cool the droplets and crystallize the aspartame. The aspartame slurry was received by the bottom portion of the crystallizer, which was surrounded by cooling jackets. The slurry was further cooled at 6 to 8° C. for 1hour and discharged. The aspartame slurry then was stirred to further crystallize as well as to facilitate the separation of solid phase aspartame crystals from liquid in the following centrifugation. The aspartame slurry thereafter was dewatered by centrifugation with 600 G-Force. Thus obtained aspartame crystals contained 38 wt. % of moisture.

EXAMPLE 2

The same experiment as in Example 1 was repeated except that the diameter of the sprayed droplets are from about 0.2 mm to about 0.3 mm. The aspartame crystals dewatered by centrifugation contained 40 wt. % of moisture.

EXAMPLE 3

The same experiment as in Example 1 was repeated except that the solvent included 25 wt % of methanol and 5.4 wt % of aspartame solution was used. The aspartame crystals dewatered by centrifugation contained 36 wt. % of moisture.

EXAMPLE 4

The same experiment as in Example 3 was repeated except that the diameter of the sprayed droplets are from about 0.4 mm to about 0.5 mm. The aspartame crystals dewatered by centrifugation contained 42 wt. % of moisture.

EXAMPLE 5

The same experiment as in Example 1 was repeated except that the cold air temperature was maintained at 10° C. and the aspartame slurry was further cooled at 15 to 20° C. The aspartame crystals dewatered by centrifugation contained 43 wt. % of moisture.

EXAMPLE 6

5.5 wt % of aspartame water solution was crystallized within a crystallizer as shown in FIG. 2. Two nozzles sprayed the aspartame solution to droplets with a diameter from about 0.1 mm to about 0.3 mm. Cold air cooled to 0° C. was blown into the crystallizer to cool the droplets and crystallize the aspartame. The aspartame slurry was received by the bottom portion of the crystallizer, which was surrounded by cooling jackets. The slurry was further cooled to 10° C. and discharged from the crystallizer. The aspartame slurry then was stirred to facilitate the separation of solid phase aspartame crystals from liquid in the following centrifugation. The aspartame slurry thereafter was dewatered by centrifugation with 600 G-Force. Thus obtained aspartame crystals contained 36 wt % of moisture.

Although the present invention has been described in terms of embodiments, other embodiments will become apparent to those of ordinary skill in the art, in view of the disclosure herein. Accordingly, the present invention is not intended to be limited by the recitation of the embodiments, but is instead intended to be defined solely by reference to the appended claims.

What is claimed is:

1. A method of crystallizing a solute dissolved in a solution, the method comprising:

preparing an aqueous solution;

blowing cold air to form a layer of cold airflow;

atomizing the solution to droplets of the solution and passing the droplets through the layer of cold air flow, thereby crystallizing the solute dissolved in the droplets; and obtaining slurry including the solute crystals and remaining solution.

2. A method as defined in claim 1, wherein the solute is α-L-aspartyl-L-phenylalanine methyl ester (aspartame), and the solution is an aqueous solution thereof.

3. A method as defined in claim 1, further comprising cooling the slurry to further crystallize the solute, which is still dissolved in the remaining solution of the slurry.

4. A method as defined in claim 3, wherein the slurry is stirred while it is being cooled.

5. A method as defined in claim 1, further comprising removing the remaining solution from the slurry to obtain solute crystals.

6. A method as defined in claim 1, wherein the droplets pass the layer of cold air flow within about 1 min.

7. A method as defined in claim 6, wherein the droplets pass the layer of cold air flow for a period of time from about 2 sec to about 30 sec.

8. A method as defined in claim 2, wherein the solution is supplied at a temperature from about 40° C. to about 70° C.

9. A method as defined in claim 8, wherein the solution is supplied at a temperature from about 50° C. to about 60° C.

10. A method as defined in claim 7, wherein the concentration of the solute is higher than about 90% of the saturated concentration at the temperature.

11. A method as defined in claim 2, wherein the cold air introduced into the chamber is at a temperature from about −5° C. to about 50° C.

12. A method as defined in claim 11, wherein the cold air introduced into the chamber is at a temperature from about 0° C. to about 20° C.

13. A method as defined in claim 1, wherein the droplets sprayed by the atomizer is sized in diameter from about 0.01 mm to about 2 mm.

14. A method as defined in claim 13, wherein the droplets sprayed by the atomizer is sized in diameter from about 0.02 mm to about 1 mm.

15. A method as defined in claim 2, wherein in the aqueous solution, the aspartame is dissolved in water or water-immiscible organic solvent.

16. A method as defined in claim 1, wherein the layer of the cold air is thicker than about 0.5 m.

17. A method as defined in claim 16, wherein the layer of the cold air is from about 1 m to about 4 m thick.

18. A method as defined in claim 1, wherein the cold air is blown at a constant speed.

19. A method as defined in claim 18, wherein the cold air flows at a slower speed than the droplets passing through the layer of the cold air.

* * * * *